United States Patent
Andersson

(10) Patent No.: US 6,697,672 B2
(45) Date of Patent: Feb. 24, 2004

(54) IMPLANTABLE HEART STIMULATOR

(75) Inventor: Jonas Andersson, Johanneshov (SE)

(73) Assignee: St. Jude Medical AB, Järfälla (SE)

( * ) Notice: Subject to any disclaimer, the term of this patent is extended or adjusted under 35 U.S.C. 154(b) by 91 days.

(21) Appl. No.: 09/937,288

(22) Filed: Sep. 24, 2001

(65) Prior Publication Data

US 2002/0095189 A1 Jul. 18, 2002

(30) Foreign Application Priority Data

Sep. 27, 2000 (SE) ................................................ 0003480

(51) Int. Cl.$^7$ ................................................ A61N 1/365
(52) U.S. Cl. ........................................ 607/17; 607/25
(58) Field of Search ........................... 128/925; 600/516, 600/517; 607/9, 17, 25

(56) References Cited

U.S. PATENT DOCUMENTS

| | | | |
|---|---|---|---|
| 4,757,815 A | | 7/1988 | Strandberg et al. ............ 607/20 |
| 5,203,326 A | | 4/1993 | Collins ............................ 607/4 |
| 5,215,098 A | | 6/1993 | Steinhaus et al. ............ 600/515 |
| 5,280,792 A | | 1/1994 | Leong et al. ................. 600/515 |
| 5,313,953 A | * | 5/1994 | Yomtov et al. ............... 128/696 |
| 5,645,575 A | | 7/1997 | Stangl et al. .................. 607/17 |
| 5,755,739 A | * | 5/1998 | Sun et al. ...................... 607/14 |
| 5,782,885 A | * | 7/1998 | Andersson ..................... 607/17 |
| 5,897,575 A | * | 4/1999 | Wickham ....................... 607/4 |
| 6,023,641 A | * | 2/2000 | Thompson ....................... 607/9 |
| 6,539,259 B1 | * | 3/2003 | Weinberg et al. ............... 607/9 |

FOREIGN PATENT DOCUMENTS

| | | | |
|---|---|---|---|
| EP | 0 449 401 | 10/1991 | .......... A61N/1/365 |
| EP | 0 465 241 | 1/1992 | .......... A61N/1/365 |
| EP | 0 653 224 | 5/1995 | .......... A61N/1/365 |
| EP | 0 882 469 | 12/1996 | ............ A61N/1/37 |
| WO | WO 98/34537 | 8/1998 | ......... A61B/5/0205 |

OTHER PUBLICATIONS

Groenewegen et al, "Database of Body Surface ECG P–Wave Integral Maps for Localization of Left–Sided Atrial Arrhythmias", US 2002/0026220–A1, Feb. 28, 2002.*

* cited by examiner

*Primary Examiner*—Carl Layno
(74) *Attorney, Agent, or Firm*—Schiff Hardin & Waite

(57) ABSTRACT

An implantable heart stimulator comprises a pulse generator (3) for delivering stimulation pulses to the heart of a patient. An IEGM means (5) registers electric signals associated with the patient's heart. A classifier means (6) classifies received electric IEGM signals according to their waveforms in at least one segment of the cardiac cycle, and a control means (4) controls the pulse generator depending on the classification of the IEGM signals. A first filtering means is provided to extract parameters related to the patient's respiration from beat-to-beat variability in the IEGM signal classification while filtering away slow classification variability extending over several cardiac cycles. The control means is adapted to receive the respiration-related parameters to control the delivery of stimulation pulses from the pulse generator depending on these parameters.

13 Claims, 3 Drawing Sheets

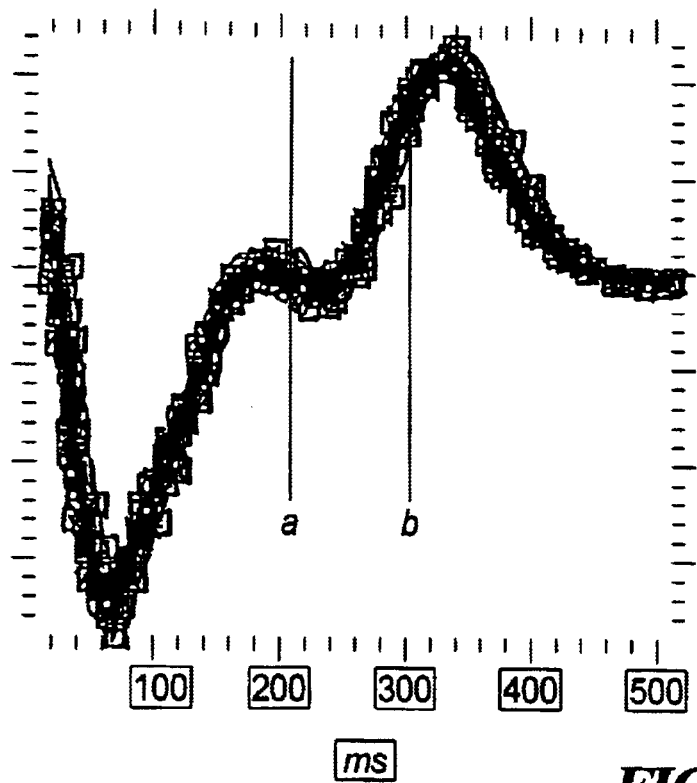
FIG. 1
FIG. 2
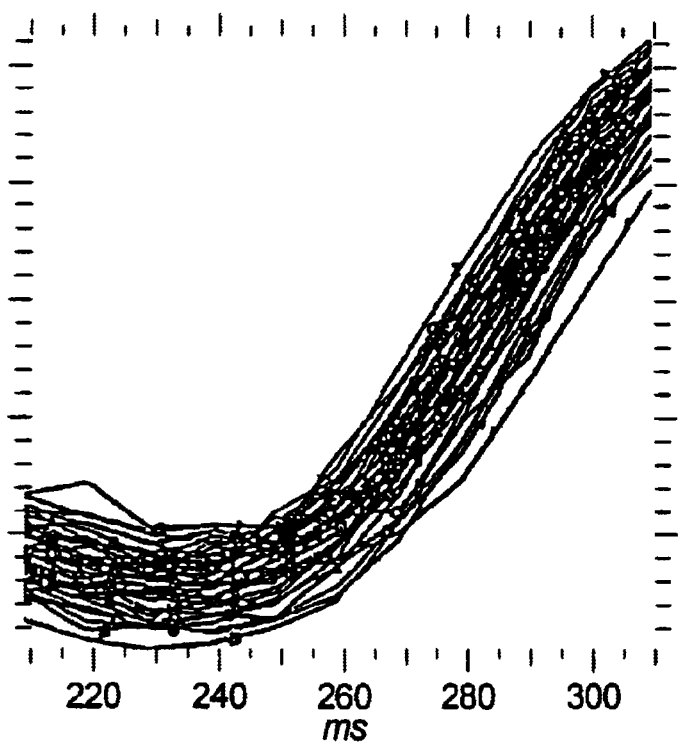

Input #

Heart Beat #

IMPLANTABLE HEART STIMULATOR

BACKGROUND OF THE INVENTION

1. Field of the Invention

The present invention relates to an implantable heart stimulator of the type having a pulse generator for delivering stimulation pulses to the heart of a patient, an IEGM unit for registering electric signals associated with the patient's heart, a classifier for classifying the received electric IEGM signals according to their waveforms in at least one segment of the cardiac cycle, and a control unit for controlling the pulse generator depending on the classification of the IEGM signals.

2. Description of the Prior Art

It is known to sense a physiologic parameter of a patient, classify the parameter, and use the information obtained for diagnostic purpose or for the purpose of treating the patient. Thus, U.S. Pat. No. 5,645,575 describes an implantable pacemaker, which senses a general physiologic parameter of the patient for use in determining the physical stress or workload of the patient. The parameter is classified and the information obtained from this classification is used to control the stimulation rate/pulse interval of the pacemaker. IEGM waveforms are not mentioned as the selected parameter to be sensed. U.S. Pat. Nos. 5,215,098 and 5,280,792 describe implantable devices, which sense IEGM signals and classify them. In the device according to U.S. Pat. No. 5,280,792 the classification results are used for adjusting the output of a cardioverter/defibrillator while the results in the device disclosed in U. S. Pat. No. 5,215,098 are used for diagnostic purposes only. In U.S. Pat. No. 5,782,885 a method and a cardiac assist system for pacing a heart of a patient are described, in which sensed IEGM signal waveforms are classified in dependence of the workload of the patient, and the results of the classification are used to control the pulse rate or stimulation interval of a pacemaker. It is also known to sense IEGM signals and classify the waveforms to use the results of this classification for identifying cardiac arrhythmias and subsequent suitable therapy, see e.g. U.S. Pat. No. 5,203,326, European Application 0 465 241 and European Application 0 653 224.

It is also known that the amplitude of the QRS complex of ordinary surface ecg:s varies with the respiration of the patient, see e.g. U.S. Pat. No. 4,757,815.

It has now been found that the waveform or morphology of IEGM:s varies with the respiration of the patient, and the present invention is based on this discovery.

SUMMARY OF THE INVENTION

An object of the invention is to provide a technique for detecting the respiration of a patient and to use the results for controlling an implantable heart stimulator.

The above object is achieved in accordance with the principles of the present invention in an implantable heart stimulator of the type initially described, wherein a filter is additionally provided to extract parameters related to the patient's respiration from beat-to-beat variability in the IEGM signal classification, while filtering out slow classification variability extending over several cardiac cycles, and also having a control unit which receives the respiration-related parameters to control delivery of stimulation pulses from the pulse generator dependent on those parameters.

Thus the beat-to-beat variability in the IEGM signal morphology is utilized to extract respiration related parameters, while slow morphology variability extending over several cardiac cycles and related to the workload is filtered away. The heart stimulator according to the invention is consequently based merely on IEGM signal processing for realizing an accurate respiration sensor, eliminating the need for mechanical sensor components. Furthermore the technique can be easily implemented in current devices.

In an embodiment of a heart stimulator according to the invention, the classifier is formed by a neural network clustering stored IEGM signals into a predetermined number of classes depending on their waveforms. By using a neural network the classification technique used is self-organizing and adaptive and can be implemented in existing devices. The neural network forms a self-organizing feature map, which can be trained to cluster the data into a predetermined number of classes.

In another embodiment of the stimulator according to the invention, the respiration related parameters are respiration rate and respiration depth. From these two parameters the minute volume can be determined and used for controlling the heart stimulator.

In another embodiment of the heart stimulator according to the invention a second filter is connected in parallel to the aforementioned filter to extract a parameter related to the workload for the patient from slow variability, extending over several cardiac cycles, in IEGM signal classification while filtering out beat-to-beat classification variability, and the control unit is adapted to receive the workload related parameter to control the delivery of stimulation pulses from the pulse generator depending on the parameter. In this way a workload and respiration dual sensor is obtained which can be used for the control of a heart stimulator. Such a dual sensor will thus extract two different control quantities, i.e. workload and respiration, from the IEGM signal.

In a further embodiment of a heart stimulator according to the invention, the first and said second filters are high pass and low pass filters respectively. In this way respiration and workload parameters can be concurrently extracted from fast, beat-to-beat variability of the classification of IEGM signals and slow variability, extending over several cardiac cycles, of the classification.

DESCRIPTION OF THE DRAWINGS

FIG. 1 is a diagram showing 60 recordings of IEGM signals from 60 paced cardiac cycles.

FIG. 2 is a diagram showing on a larger scale a portion of the IEGM:s shown in FIG. 1 corresponding to the ST-T segment of the ordinary surface ecg.

DESCRIPTION OF THE PREFERRED EMBODIMENTS

FIG. 1 shows 60 IEGM:s recorded by a bipolar lead from a patient paced at a fixed heart rate of 70 bpm. The lead was positioned in the ventricle and both sampling and stimulation were performed via the same lead [in the same way] as described in the above-mentioned U.S. Pat. No. 5,782,885. The patient was resting.

Figure 4:
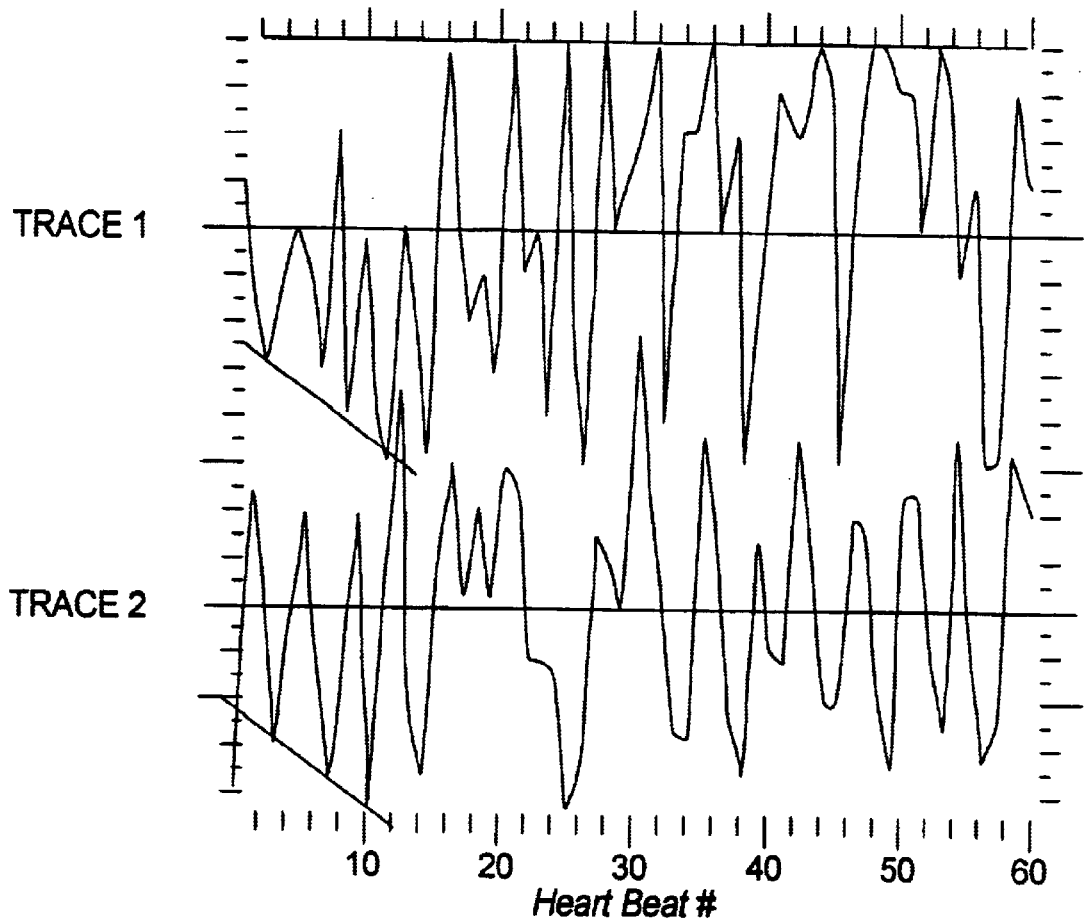
FIG. 4 shows the time evolution of the classification output obtained from the SOFM and the time evolution of the signal from a fast thermistor positioned in one nostril of a patient when recording the IEGM:s.

During these measurements the temperature of the patient's expired breath at one nostril was measured by a fast reacting thermistor to directly monitor the respiration of the patient and get an estimate of both respiration rate and depth, cf. FIG. 4.

A self-organizing feature map (SOFM) was applied to a window of about 100 ms of the recorded IEGM substantially corresponding to the ST-T segment of corresponding surface ecg:s, delimited by the vertical lines a and b in FIG. 1 and shown in a larger scale in FIG. 2. The SOFM algorithm used in this example had 11 input nodes and 10 output nodes. Each input node corresponds to an amplitude sample in the ST-T segment, i.e. a sampling rate of 100 samples/s. The output nodes correspond to different morphological classification of the input signal, cf. also the technique described in the above-mentioned U.S. Pat. No. 5,782,885.

Figure 3:
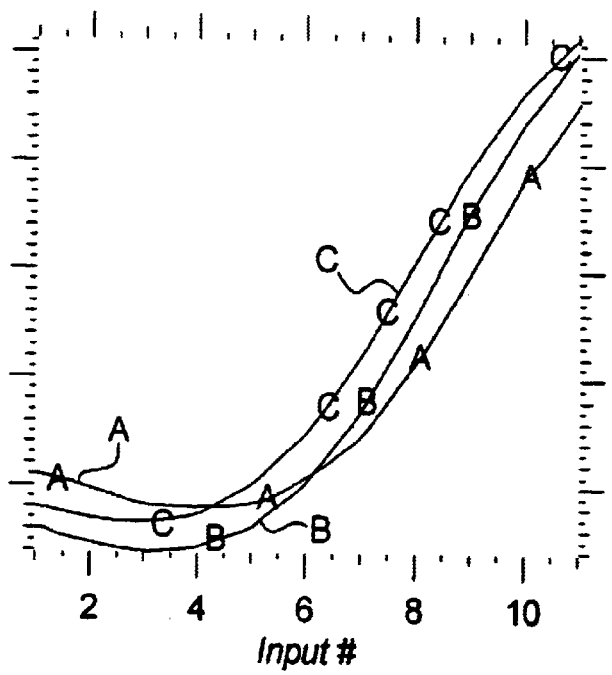
FIG. 3 is a diagram showing the two end maps and the midpoint map obtained by applying a self-organizing feature map (SOFM) algorithm to the signals in FIG. 2.

The SOFM algorithm converges to a low mean error that is a prerequisite for accurate map formation. In FIG. 3 the two end-maps and the midpoint map (curve B) obtained from the data of FIG. 2 are plotted, curve A and curve C being the respective end-maps. FIG. 3 shows the existence of a valid topological relation between the morphology represented by the different output nodes from the SOFM.

When the recorded 60 IEGM:s were classified by the SFOM algorithm it was found that the classification varied with the number of the heart beat as shown in the trace 1 in FIG. 4. Trace 2 in FIG. 4 shows the corresponding curve obtained from the signals from a fast thermistor positioned in one nostril of the patient. From FIG. 4 it can be seen that traces 1 and 2 are correlated, i.e. the IEGM SOFM output is related to the respiration.

The respiration rate is directly deductible from FIG. 4, however, FIG. 4 also comprises information about respiration depth, see e.g. the trend indicated by the slanted line during the first 10 cardiac cycles. By forming the product of a number of zero-crossings and the average peak amplitude during a specified period of time of trace c in FIG. 4 a quantity is obtained which corresponds to the minute volume. Thus with the present invention it is possible to obtain a quantity corresponding to the minute ventilation for use in controlling the pulse generator. Of course obtained values of the respiration rate can be directly used in the control of the heart stimulator, if appropriate.

By using a SOFM technique as described above the set-up of the sensor is obtained automatically and it will be adapted, i.e. it may track long-term alterations of the IEGM. The number of classes can be adapted to measured data. If these data comprise a plurality of classes representing different phases of the respiratory cycle, the SOFM may be trained to cluster the data into e.g. 20 classes, each class relating to a specific phase of the respiratory cycle. Subsequent unknown IEGM signals will then be classified into one of these 20 classes.

Since the morphology is changed somewhat when the stimulation rate is changed, a workload-stimulation rate matrix in analogy to what is disclosed in the above-mentioned U.S. Pat. No. 5,782,885 is needed. Alternatively, a 2-dimensional feature map can be used.

For the SOFM a neural network of the kind described in U.S. Pat. No. 5,782,885 is preferably used for clustering IEGM signals into a predetermined number of classes based on morphological similarities.

Figure 5:
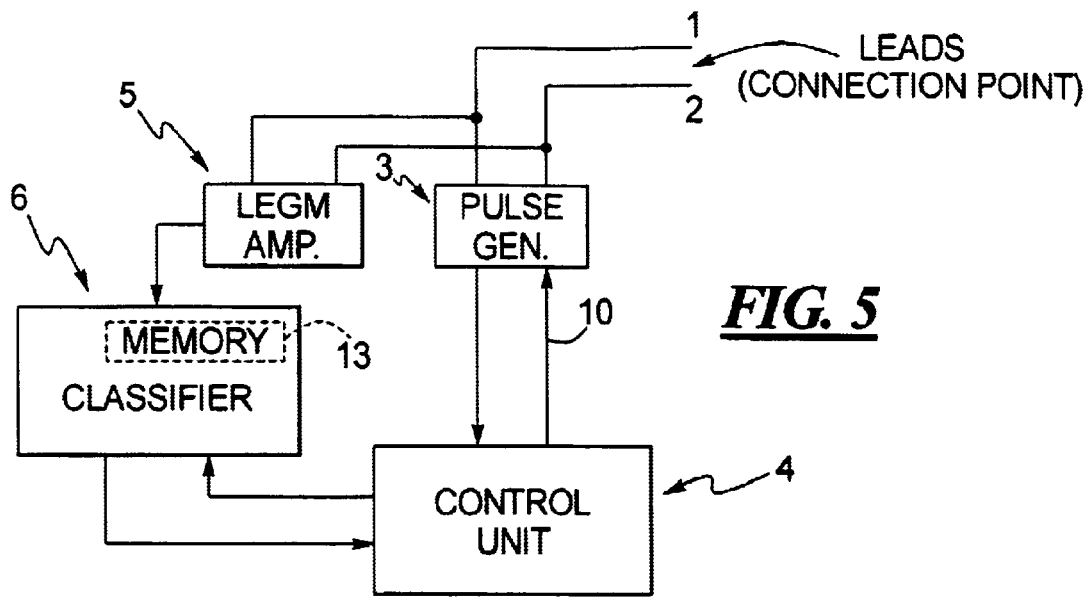
FIG. 5 is a schematic block diagram of an embodiment of an implantable heart stimulator according to the invention.

FIG. 5 shows an embodiment of the implantable heart stimulator according to the invention. Connected to the input terminals 1 and 2 of the unipolar or bipolar lead is a pulse generator 3, shown as a functional block. This block contains circuitry for generating the stimulation pulses. The block also contains circuitry for interfacing with the control unit 4, which is controlling the delivery of stimulation pulses from the pulse generator.

The heart stimulator also includes an IEGM amplifier 5 for amplification and filtering of the IEGM signal. The amplifier 5 is connected to the input terminals for receiving IEGM signals from connectable implanted leads and for amplifying IEGM signals.

The signals from the amplifier 5 are supplied to a classifier 6. Its function is to classify the recorded IEGM:s into different morphological groups or classes. The classifying function can be implemented in several different ways both with regard to the underlying algorithms and the hardware used, cf. the above-mentioned U.S. Pat. No. 5,782,885.

A memory 13 is provided for storing signal waveforms from a number of received IEGM signals and the classifier 6 is adapted to classify a current IEGM signal by matching its waveform to one of the stored signal waveforms, by using e.g. pattern recognition algorithms. As explained above the classifier 6 preferably is a neural network clustering stored IEGM signals into predetermined number of classes depending of their waveforms. IEGM signals supplied to the neural network are then encoded and stored in the memory 13 in encoded formed for subsequent classification use.

The control unit 4 interprets the classification results from the classifier 6 and based thereon sends control signals to a control input 10 of the pulse generator 3.

Figure 6:
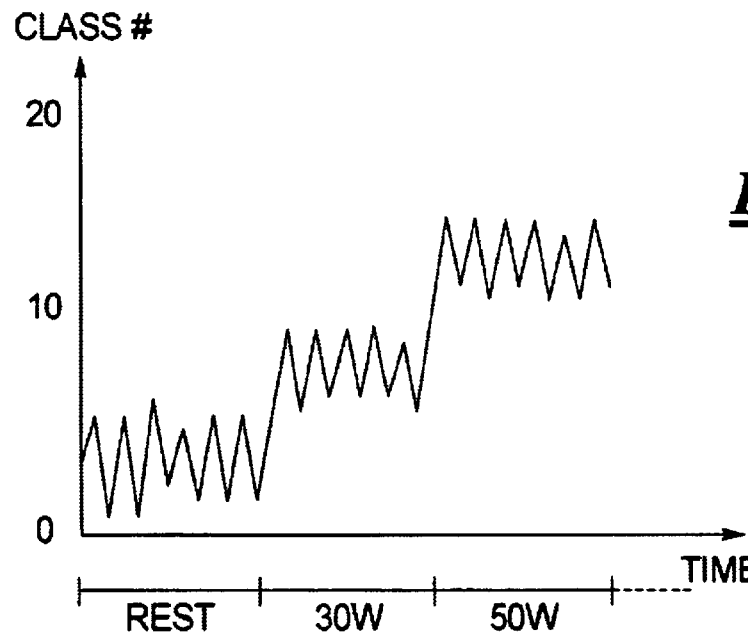
FIG. 6 is a diagram illustrating principally the variation in classification of IEGM:s recorded for different workloads.

FIG. 6 illustrates qualitatively the variation of the classification obtained by the above described technique as a function of time for different workload levels, viz. rest, 30 W and 50 W. As can be seen from FIG. 6 a changed workload results in a change of the IEGM classification. On this slow, workload-depending variability of the classification a faster, beat-to-beat variability is superposed. This beat-to-beat variability is caused by the respiration as described above. These two kinds of IEGM classification variability make design of a respiration and workload dual sensor possible based exclusively on IEGM signal processing.

Figure 7:
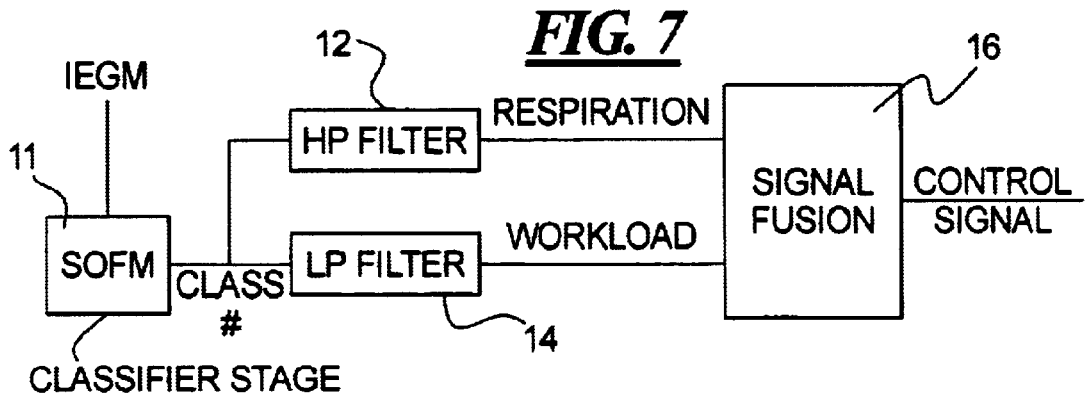
FIG. 7 is a block-diagram showing the basic structure of a respiration and workload dual sensor of the heart stimulator according to the invention.

FIG. 7 shows the structure of such a dual sensor, which can be implemented in the heart stimulator according to the invention as the classifier 6. Thus recorded IEGM:s are classified in a classifier stage 11 by using a SOFM algorithm, preferably in the form of a neural network. The output signal from the classifier stage 11 is supplied to a high pass filter 12 and a low pass filter 14 connected in parallel. The high pass filter 12 is adapted to extract parameters related to the patient's respiration from beat-to-beat variability in the IEGM classification while filtering away slow classification variability extending over several cardiac cycles, whereas the low pass filter 14 is adapted to extract the parameter related to workload for the patient from the slow variability, while filtering away beat-to-beat variability. The resulting respiration related and workload related parameters are respectively supplied to a signal fusion unit 16 which generates an output signal depending on the values of these supplied parameters. This output signal is used as a control signal for the pulse generator.

The signal fusion unit 16 can be realized in many different ways, e.g. in analogy with known, so called MV-activity combined sensors. Such a sensor combines a minute volume (MV) sensor with a workload activity sensor. In this known sensors the minute volume is determined from measurements of the impedance across the patient's thorax by means of electric current pulses. Since the impedance varies during the respiration cycle the minute volume can be estimated in this way. As a workload sensor an accelerometer is used which determines the movement of the patient's body. The minute volume signal and the workload signal are then combined, preferably by using so-called fuzzy logic means for controlling the stimulation rate of a pacemaker.

Above, the invention is described in connection with a state of complete stimulation, i.e. each heart beat is a stimulated heart beat. The technique according to the invention can, however, also be used in a state of spontaneous heart activity of the patient. For patients suffering form e.g. chronotropic incompetence, i.e. the heart exhibits spontaneous activity but the heart rate is not increasing sufficiently in case of increasing workload of the patient, a heart stimulator according to the invention could be an useful aid.

Although modifications and changes may be suggested by those skilled in the art, it is the intention of the inventor to embody within the patent warranted hereon all changes and modifications as reasonably and properly come within the scope of his contribution to the art.

I claim:

1. An implantable heart stimulator comprising:
   a pulse generator which emits stimulation pulses adapted for delivery to a heart of a patient;
   an IEGM unit adapted to obtain and register electrical IEGM signals from the heart, said IEGM signals having waveforms associated therewith;
   a classifier connected to the IEGM unit for receiving the IEGM signals therefrom and for classifying the received IEGM signals according to their waveforms in at least one segment of a cardiac cycle, thereby producing classified IEGM signals, said classified IEGM signals containing beat-to-beat variability, and slow variability extending over several cardiac cycles;
   a filter connected to said classifier and supplied with said classified IEGM signals, said filter extracting parameters related to respiration of the patient from said beat-to-beat variability in the classified IEGM signals and filtering out said slow variability; and
   a control unit supplied with said parameters and connected to said pulse generator for controlling delivery of said stimulation pulses from said pulse generator dependent on said parameters.

2. A heart stimulator as claimed in claim 1 further comprising a memory connected to said classifier in which signal waveforms are stored from a plurality of received IEGM signals, for use by said classifier in classifying subsequently received IEGM signals.

3. A heart stimulator as claimed in claim 2 wherein said classifier classifies a subsequently received IEGM signal by matching the waveform of the subsequently received IEGM signal to one of said signal waveforms stored in said memory.

4. A heart stimulator as claimed in claim 3 wherein said classifier employs a pattern recognition algorithm for said matching.

5. A heart stimulator as claimed in claim 2 wherein said memory also stores said IEGM signals respectively associated with said signal waveforms, and wherein said classifier comprises a neural network which clusters the stored IEGM signals into a predetermined number of classes dependent on their respective waveforms.

6. A heart stimulator as claimed in claim 5 wherein said neural network receives said IEGM signals and encodes their respective waveforms, to obtain encoded waveforms, and wherein said memory stores said encoded waveforms as said signal waveforms.

7. A heart stimulator as claimed in claim 1 wherein said classifier classifies said received IEGM signals according to their respective waveforms in signal segments corresponding to an ST interval of an ordinary ECG.

8. A heart stimulator as claimed in claim 7 wherein said classifier employs a signal segment having a length of approximately 100 msec.

9. A heart stimulator as claimed in claim 1 wherein said classifier classifies said received IEGM signals according to their respective waveforms in signal segments corresponding to a T-wave of an ordinary ECG.

10. A heart stimulator as claimed in claim 1 wherein said parameters related to respiration extracted by said filter are respiration rate and respiration depth.

11. A heart stimulator as claimed in claim 1 wherein said filter is a first filter, and wherein said heart stimulator further comprises a second filter connected to said classifier in parallel with said first filter to also receive said classified IEGM signals, said second filter extracting a further parameter related to a workload of the patient from said slow variability and filtering out said beat-to-beat variability, and wherein said control unit also receives said further parameter from said second filter and controls delivery of said stimulation pulses from said pulse generator dependent on said parameter and said further parameter.

12. A heart stimulator as claimed in claim 11 wherein said first filter is a high-pass filter and wherein said second filter is a low-pass filter.

13. A heart stimulator as claimed in claim 1 wherein said filter is a high-pass filter.

* * * * *